United States Patent
Battiste et al.

(10) Patent No.: US 7,213,413 B2
(45) Date of Patent: May 8, 2007

(54) NONINVASIVE MEASUREMENT AND CONTROL SYSTEM FOR USE IN HYDROCARBON PROCESSING

(75) Inventors: David R. Battiste, Conroe, TX (US); Donald L. Andress, Houston, TX (US)

(73) Assignee: Conocophillips Company, Houston, TX (US)

( * ) Notice: Subject to any disclaimer, the term of this patent is extended or adjusted under 35 U.S.C. 154(b) by 327 days.

(21) Appl. No.: 10/869,600

(22) Filed: Jun. 16, 2004

(65) Prior Publication Data

US 2005/0279131 A1   Dec. 22, 2005

(51) Int. Cl.
*F25J 3/00* (2006.01)
*F25J 1/00* (2006.01)
*G01J 3/44* (2006.01)

(52) U.S. Cl. .................. 62/628; 62/612; 356/301
(58) Field of Classification Search .......... 62/620, 62/628, 612; 356/301
See application file for complete search history.

(56) References Cited

U.S. PATENT DOCUMENTS

| | | | |
|---|---|---|---|
| 2,774,715 A * | 12/1956 | Gilmore ................. 208/351 |
| 4,783,168 A | 11/1988 | Florisson et al. | |
| 5,110,204 A | 5/1992 | Miles et al. | |
| 5,652,653 A * | 7/1997 | Alsmeyer et al. ........ 356/301 |
| 5,684,580 A * | 11/1997 | Cooper et al. .......... 356/301 |
| 5,712,481 A | 1/1998 | Welch et al. | |
| 5,724,833 A | 3/1998 | Devers | |
| 5,737,940 A | 4/1998 | Yao et al. | |
| 5,751,415 A | 5/1998 | Smith et al. | |
| 5,822,058 A | 10/1998 | Adler-Golden et al. | |
| 5,892,228 A | 4/1999 | Cooper et al. | |
| 5,982,484 A | 11/1999 | Clarke et al. | |
| 6,028,667 A | 2/2000 | Smith et al. | |
| 6,100,975 A * | 8/2000 | Smith et al. ............ 356/301 |
| 6,112,549 A * | 9/2000 | Yao et al. .............. 62/620 |
| 6,140,647 A * | 10/2000 | Welch et al. ......... 250/339.12 |
| 6,881,381 B1 * | 4/2005 | Asher et al. ............ 422/68.1 |
| 2003/0048450 A1 * | 3/2003 | Pope et al. ............. 356/435 |

* cited by examiner

*Primary Examiner*—William C. Doerrler
(74) *Attorney, Agent, or Firm*—Hovey Williams LLP (57) ABSTRACT

Raman spectrometers are employed in a hydrocarbon processing plant for online measurement of at least one compositional property of a hydrocarbon stream. The Raman spectrometers can be used to control separations equipment, determine energy content, and/or determine flow rate. The Raman spectrometers are especially advantageous when employed in a liquefied natural gas (LNG) plant to determine properties of cooled natural gas streams.

63 Claims, 5 Drawing Sheets

NONINVASIVE MEASUREMENT AND CONTROL SYSTEM FOR USE IN HYDROCARBON PROCESSING

BACKGROUND OF THE INVENTION

1. Field of the Invention

The present invention relates generally to measurement systems for determining various compositional properties of hydrocarbon streams. In another aspect, the invention concerns the use of noninvasive measurement systems in liquefied natural gas (LNG) plants to more effectively measure compositional and/or flow properties of cooled natural gas streams. In still another aspect, the invention concerns the use of noninvasive measurement systems to more effectively control separation equipment employed in a LNG plant.

2. Description of the Prior Art

It is common practice to cryogenically liquefy natural gas for transport and storage. The primary reason for the liquefaction of natural gas is that liquefaction results in a volume reduction of about 1/600, thereby making it possible to store and transport the liquefied gas in containers of more economical and practical design. For example, when gas is transported by pipeline from the source of supply to a distant market, it is desirable to operate the pipeline under a substantially constant and high load factor. Often the deliverability or capacity of the pipeline will exceed demand while at other times the demand may exceed the deliverability of the pipeline. In order to shave off the peaks where demand exceeds supply, it is desirable to store the excess gas in such a manner that it can be delivered when the supply exceeds demand, thereby enabling future peaks in demand to be met with material from storage. One practical means for doing this is to convert the gas to a liquefied state for storage and to then vaporize the liquid as demand requires.

Liquefaction of natural gas is of even greater importance in making possible the transport of gas from a supply source to market when the source and market are separated by great distances and a pipeline is not available or is not practical. This is particularly true where transport must be made by ocean-going vessels. Ship transportation in the gaseous state is generally not practical because appreciable pressurization is required to significantly reduce the specific volume of the gas which in turn requires the use of more expensive storage containers.

In order to store and transport natural gas in the liquid state, the natural gas is preferably cooled to $-240°$ F. to $-260°$ F. where it possesses a near-atmospheric vapor pressure. Numerous systems exist in the prior art for the liquefaction of natural gas by sequentially passing the gas at an elevated pressure through a plurality of cooling stages whereupon the gas is cooled to successively lower temperatures until the liquefaction temperature is reached. Cooling is generally accomplished by heat exchange with one or more refrigerants such as propane, propylene, ethane, ethylene, and methane or a combination of one or more of the preceding. In the art, the refrigerants are frequently arranged in a cascaded manner and each refrigerant is employed in a closed refrigeration cycle. Further cooling of the liquid is possible by expanding the liquefied natural gas to atmospheric pressure in one or more expansion stages. In each stage, the liquefied gas is flashed to a lower pressure thereby producing a two-phase gas-liquid mixture at a significantly lower temperature. The liquid is recovered and may again be flashed. In this manner, the liquefied gas is further cooled to a storage or transport temperature suitable for liquefied gas storage at near-atmospheric pressure. In this expansion to near-atmospheric pressure, some additional volumes of liquefied gas are flashed. The flashed vapors from the expansion stages are generally collected and recycled for liquefaction or utilized as fuel gas for power generation.

A significant problem in the liquefaction of natural gas is that of accurately measuring compositional properties of the various cooled natural gas streams within or exiting the liquefied natural gas (LNG) plant. In the past, measurement of the compositional properties of cooled natural gas in a LNG plant was typically accomplished by extracting a sample of the natural gas and then using gas chromatography to determine its constituent parts. This sampling and analysis process was difficult and hazardous when the sampled streams included mixtures of methane, ethane, and propane at temperatures of less than $-100°$ C. and pressures of 50 to 150 bars absolute, which are typical conditions in a LNG plant. It was also difficult to obtain consistent, repeatable analysis under the operating conditions of an LNG plant due to the error introduced during sampling and subsequent conversion to vapor for analysis.

Another common problem encountered in the production of LNG is that of measuring the rate of LNG production from the plant. Accurate flow measurement of produced LNG is very important for determining the overall performance of the plant. One conventional system for measuring the rate of LNG production employs a float in the LNG storage tank. Changes in elevation of the float in the LNG storage tank can be used to estimate the flow rate of LNG into the tank. However, this method of determining the flow rate of LNG from a plant is subject to many sources of error.

Another problem encountered in the production, transportation, and sale of LNG is that of determining the energy content (i.e., BTU content) of LNG for custody transfer purposes. Conventional sampling and analysis procedures for determining energy content have many associated errors. As such, the measured energy content of liquefied natural gas can vary by as much as 5% due to sampling and analysis error. This can be a particularly significant problem when bonus payments are contingent upon energy content-related performance guarantees.

A further problem in the liquefaction of natural gas is the removal of residual amounts of benzene, cyclohexane, and other aromatic compounds (i.e., heavies) from the natural gas stream immediately prior to the liquefaction of the natural gas stream. These heavy hydrocarbon components tend to precipitate and solidify thereby causing fouling and potential plugging of pipes and key process equipment. As an example, such fouling can significantly reduce the heat transfer efficiency and throughput of heat exchangers, particularly plate-fin heat exchangers. Conventional methods for removing heavies from natural gas in a LNG plant employ a heavies removal column that operates near the critical point of the natural gas stream. The temperature in the heavies removal column is typically controlled by measuring the temperature in the column and then adjusting the flow rate of a stripping gas to the column based on the measured temperature. However, simply measuring the temperature in the heavies removal column is only an indirect indicator of whether a sufficient amount of heavy hydrocarbon components are being removed from the natural gas. Thus, current control systems for removing heavies from natural gas in a LNG plant are relatively insensitive to the actual amount of heavies being removed.

OBJECTS AND SUMMARY OF THE INVENTION

It is, therefore, an object of the present invention to provide a system for more effectively measuring the compositional properties of hydrocarbon streams, particularly cooled natural gas streams.

Another object of the invention is to provide a system for more effectively determining the flow rate of a fluid stream through a conduit.

Yet another object of the invention is to provide a system for more effectively measuring the energy content of hydrocarbon streams, such as LNG.

A further object of the invention is to provide a more effective system for removing heavy hydrocarbon compounds from natural gas in a LNG plant.

It should be noted that the above-listed objects of the invention need not all be accomplished by the invention claimed herein. In addition, other objects and advantages of the present invention are readily recognizable by one skilled in the art in view of the following detailed description of the preferred embodiments, drawing figures, and claims.

In one embodiment of the present invention, there is provided a method of liquefying natural gas comprising the steps of: (a) cooling the natural gas to thereby produce a cooled natural gas having a temperature of less than about −25° F.; (b) transporting the cooled natural gas in a conduit; and (c) while the cooled natural gas is flowing through the conduit, using a Raman spectrometer to measure at least one property of the cooled natural gas without removing the cooled natural gas from the conduit.

In another embodiment of the invention, there is provided a method of separating a heavy hydrocarbon from a light hydrocarbon comprising the steps of: (a) charging a hydrocarbon-containing stream comprising the heavy hydrocarbon and the light hydrocarbon to a separator; (b) in the separator, separating the hydrocarbon-containing stream into a light hydrocarbon-rich stream and a heavy hydrocarbon-rich stream; (c) using a Raman spectrometer to analyze the light hydrocarbon-rich stream and determine a measured heavy hydrocarbon value indicative of the amount of the heavy hydrocarbon in the light hydrocarbon stream; and (d) adjusting at least one operating parameter of the separator in response to the measured heavy hydrocarbon value.

In still another embodiment of the invention, there is provided a method of measuring the velocity of a fluid stream flowing through a conduit comprising the steps of: (a) injecting a marker into the fluid stream flowing through the conduit at an injection location; (b) using a first Raman spectrometer to detect the presence of the marker in the fluid stream at a first measurement location downstream of the injection location; and (c) using a second Raman spectrometer to detect the presence of the marker in the fluid stream at a second measurement location downstream of the first measurement location.

In yet another embodiment of the invention, there is provided a method of controlling a heavies removal column in a liquefied natural gas plant comprising the steps of: (a) charging a natural gas stream comprising a light hydrocarbon and a heavy hydrocarbon to the heavies removal column; (b) simultaneously with step (a), charging a stripping gas stream to the heavies removal column; (c) in the heavies removal column, separating the natural gas stream into a light hydrocarbon-rich stream and a heavy hydrocarbon-rich stream; (d) using a Raman spectrometer to determine a measured heavy hydrocarbon value indicative of the amount of the heavy hydrocarbon in the light hydrocarbon-rich stream; and (e) adjusting the flow rate of the stripping gas to the heavies removal column in response to the measured heavy hydrocarbon value.

In a further embodiment of the present invention, there is provided an apparatus for liquefying natural gas. The apparatus comprises a final refrigeration cycle for producing liquefied natural gas at a temperature less than about −25° F., a conduit for carrying the produced liquefied natural gas away from the final refrigeration cycle, and a first Raman spectrometer coupled to the conduit and operable to measure at least one compositional property of the liquefied natural gas without removing the liquefied natural gas from the conduit.

In a still further embodiment of the present invention, there is provided an apparatus for liquefying natural gas. The apparatus comprises a heavies removal column operable to remove at least one heavy hydrocarbon from the natural gas, a stripping gas conduit fluidly coupled to the heavies removal column and operable to deliver a stripping gas to the heavies removal column, a flow controller operable to control the flow of the stripping gas to the heavies removal column, a Raman spectrometer disposed downstream of the heavies removal column and operable to detect the heavy hydrocarbon in the natural gas stream and generate a signal indicative of the amount of the heavy hydrocarbon in the natural gas stream, and an automatic control device operably coupled to the flow controller and the Raman spectrometer. The automatic control device is programmed to adjust the flow controller in response to the signal generated by the Raman spectrometer.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENT

As used herein, the term open-cycle cascaded refrigeration process refers to a cascaded refrigeration process comprising at least one closed refrigeration cycle and one open refrigeration cycle where the boiling point of the refrigerant/cooling agent employed in the open cycle is less than the boiling point of the refrigerating agent or agents employed in the closed cycle(s) and a portion of the cooling duty to condense the compressed open-cycle refrigerant/cooling agent is provided by one or more of the closed cycles. In the current invention, methane or a predominately methane stream is employed as the refrigerant/cooling agent in the open cycle. This stream is comprised of the processed natural gas feed stream and the compressed open methane cycle gas streams.

The design of a cascaded refrigeration process involves a balancing of thermodynamic efficiencies and capital costs. In heat transfer processes, thermodynamic irreversibilities are reduced as the temperature gradients between heating and cooling fluids become smaller, but obtaining such small temperature gradients generally requires significant increases in the amount of heat transfer area, major modifications to various process equipment and the proper selection of flowrates through such equipment so as to ensure that both flowrates and approach and outlet temperatures are compatible with the required heating/cooling duty.

One of the most efficient and effective means of liquefying natural gas is via an optimized cascade-type operation in combination with expansion-type cooling. Such a liquefaction process is comprised of the sequential cooling of a natural gas stream at an elevated pressure, for example about 600 to about 2,500 psia, by sequentially cooling the gas stream via passage through a multistage propane cycle, a multistage ethane or ethylene cycle, and an open-end methane cycle which utilizes a portion of the feed gas as a source of methane and which includes therein a multistage expansion cycle to further cool the same and reduce the pressure to near-atmospheric pressure. In the sequence of cooling cycles, the refrigerant having the highest boiling point is utilized first followed by a refrigerant having an intermediate boiling point and finally by a refrigerant having the lowest boiling point. As used herein, the term "propane chiller" shall denote a cooling system that employs a refrigerant having a boiling point the same as, or similar to, that of propane or propylene. As used herein, the term "ethylene chiller" shall denote a cooling system that employs a refrigerant having a boiling point the same as, or similar to, that of ethane or ethylene. As used herein, the terms "upstream" and "downstream" shall be used to describe the relative positions of various components of a natural gas liquefaction plant along the flow path of natural gas through the plant.

Various pretreatment steps provide a means for removing undesirable components, such as acid gases, mercaptans, mercury, moisture, and heavier hydrocarbon condensate from the natural gas feed stream delivered to the facility. The composition of this gas stream may vary significantly. As used herein, a natural gas stream is any stream principally comprised of methane which originates in major portion from a natural gas feed stream, such feed stream for example containing at least 85 mole percent methane, with the balance being ethane, higher hydrocarbons, nitrogen, carbon dioxide and a minor amounts of other contaminants such as mercury, hydrogen sulfide, and mercaptans. The pretreatment steps may be separate steps located either upstream of the cooling cycles or located downstream of one of the early stages of cooling in the initial cycle. The following is a non-inclusive listing of some of the available means which are readily available to one skilled in the art. Acid gases and to a lesser extent mercaptans are routinely removed via a chemical reaction process employing an aqueous amine-bearing solution. This treatment step is generally performed upstream of the cooling stages in the initial cycle. A major portion of the water is routinely removed as a liquid via two-phase gas-liquid separation following gas compression and cooling upstream of the initial cooling cycle and also downstream of the first cooling stage in the initial cooling cycle. Mercury is routinely removed via mercury sorbent beds. Residual amounts of water and acid gases are routinely removed via the use of properly selected sorbent beds such as regenerable molecular sieves.

The pretreated natural gas feed stream is generally delivered to the liquefaction process at an elevated pressure or is compressed to an elevated pressure, that being a pressure greater than 500 psia, preferably about 500 psia to about 3,000 psia. The stream temperature is typically near ambient to slightly above ambient. A representative temperature range being 60° F. to 140° F.

As previously noted, the natural gas feed stream is cooled in a plurality of multistage (for example, three) cycles or steps by indirect heat exchange with a plurality of refrigerants, preferably three. The overall cooling efficiency for a given cycle improves as the number of stages increases but this increase in efficiency is accompanied by corresponding increases in net capital cost and process complexity. The feed gas is preferably passed through an effective number of refrigeration stages, nominally two, preferably two to four, and more preferably three stages, in the first closed refrigeration cycle utilizing a relatively high boiling refrigerant. Such refrigerant is preferably comprised in major portion of propane, propylene or mixtures thereof, more preferably the refrigerant comprises at least about 75 mole percent propane, still more preferably at least 90 mole percent propane, and most preferably the refrigerant consists essentially of propane. Thereafter, the processed feed gas flows through an effective number of stages, nominally two, preferably two to four, and more preferably two or three, in a second closed refrigeration cycle in heat exchange with a refrigerant having a lower boiling point. Such refrigerant is preferably comprised in major portion of ethane, ethylene or mixtures thereof, more preferably the refrigerant comprises at least about 75 mole percent ethylene, more preferably at least 90 mole percent ethylene, and most preferably the refrigerant consists essentially of ethylene. Each cooling stage comprises a separate cooling zone. As previously noted, the processed natural gas feed stream is combined with one or more recycle streams (i.e., compressed open methane cycle gas streams) at various locations in the second cycle thereby producing a liquefaction stream. In the last stage of the second cooling cycle, the liquefaction stream is condensed (i.e., liquefied) in major portion, preferably in its entirety thereby producing a pressurized LNG-bearing stream. Generally, the process pressure at this location is only slightly lower than the pressure of the pretreated feed gas to the first stage of the first cycle.

Generally, the natural gas feed stream will contain such quantities of $C_2+$ components so as to result in the formation of a $C_2+$ rich liquid in one or more of the cooling stages. This liquid is removed via gas-liquid separation means, preferably one or more conventional gas-liquid separators. Generally, the sequential cooling of the natural gas in each stage is controlled so as to remove as much as possible of the $C_2$ and higher molecular weight hydrocarbons from the gas to produce a gas stream predominating in methane and a liquid stream containing significant amounts of ethane and heavier components. An effective number of gas/liquid separation means are located at strategic locations downstream of the cooling zones for the removal of liquids streams rich in $C_2+$ components. The exact locations and number of gas/liquid separation means, preferably conventional gas/liquid separators, will be dependant on a number of operating parameters, such as the $C_2+$ composition of the natural gas feed stream, the desired BTU content of the LNG product, the value of the $C_2+$ components for other applications and other factors routinely considered by those skilled in the art of LNG plant and gas plant operation. The $C_2+$ hydrocarbon stream or streams may be demethanized via a single stage flash or a fractionation column. In the latter case, the resulting methane-rich stream can be directly returned at pressure to the liquefaction process. In the former case, this methane-rich stream can be repressurized and recycle or can be used as fuel gas. The $C_2+$ hydrocarbon stream or streams or the demethanized $C_2+$hydrocarbon stream may be used as fuel or may be further processed such as by fractionation in one or more fractionation zones to produce individual streams rich in specific chemical constituents (ex., $C_2$, $C_3$, $C_4$ and $C_5+$).

The pressurized LNG-bearing stream is then further cooled in a third cycle or step referred to as the open methane cycle via contact in a main methane economizer with flash gases (i.e., flash gas streams) generated in this third cycle in a manner to be described later and via expansion of the pressurized LNG-bearing stream to near atmospheric pressure. Flashing of the pressurized LNG-bearing stream, preferably a liquid stream, to near atmospheric pressure produces an LNG product possessing a temperature of −240° F. to −260° F. The flash gases used as a refrigerant in the third refrigeration cycle are preferably comprised in major portion of methane, more preferably the refrigerant comprises at least about 75 mole percent methane, still more preferably at least 90 mole percent methane, and most preferably the refrigerant consists essentially of methane. During expansion of the pressurized LNG-bearing stream to near atmospheric pressure, the pressurized LNG-bearing stream is cooled via at least one, preferably two to four, and more preferably three expansions where each expansion employs as a pressure reduction means either Joule-Thomson expansion valves or hydraulic expanders. The expansion is followed by a separation of the gas-liquid product with a separator. When a hydraulic expander is employed and properly operated, the greater efficiencies associated with the recovery of power, a greater reduction in stream temperature, and the production of less vapor during the flash step will frequently more than off-set the more expensive capital and operating costs associated with the expander. In one embodiment, additional cooling of the pressurized LNG-bearing stream prior to flashing is made possible by first flashing a portion of this stream via one or more hydraulic expanders and then via indirect heat exchange means employing said flash gas stream to cool the remaining portion of the pressurized LNG-bearing stream prior to flashing. The warmed flash gas stream is then recycled via return to an appropriate location, based on temperature and pressure considerations, in the open methane cycle and will be recompressed.

Critical to the liquefaction of natural gas in a cascaded process is the use of one or more refrigerants for transferring heat energy from the natural gas stream to the refrigerant and ultimately transferring said heat energy to the environment. In essence, the overall refrigeration system functions as a heat pump by removing heat energy from the natural gas stream as the stream is progressively cooled to lower and lower temperatures.

The liquefaction process may use one of several types of cooling which include but is not limited to (a) indirect heat exchange, (b) vaporization, and (c) expansion or pressure reduction. Indirect heat exchange, as used herein, refers to a process wherein the refrigerant cools the substance to be cooled without actual physical contact between the refrigerating agent and the substance to be cooled. Specific examples of indirect heat exchange means include heat exchange undergone in a shell-and-tube heat exchanger, a core-in-kettle heat exchanger, and a brazed aluminum plate-fin heat exchanger. The physical state of the refrigerant and substance to be cooled can vary depending on the demands of the system and the type of heat exchanger chosen. Thus, a shell-and-tube heat exchanger will typically be utilized where the refrigerating agent is in a liquid state and the substance to be cooled is in a liquid or gaseous state or when one of the substances undergoes a phase change and process conditions do not favor the use of a core-in-kettle heat exchanger. As an example, aluminum and aluminum alloys are preferred materials of construction for the core but such materials may not be suitable for use at the designated process conditions. A plate-fin heat exchanger will typically be utilized where the refrigerant is in a gaseous state and the substance to be cooled is in a liquid or gaseous state. Finally, the core-in-kettle heat exchanger will typically be utilized where the substance to be cooled is liquid or gas and the refrigerant undergoes a phase change from a liquid state to a gaseous state during the heat exchange.

Vaporization cooling refers to the cooling of a substance by the evaporation or vaporization of a portion of the substance with the system maintained at a constant pressure. Thus, during the vaporization, the portion of the substance which evaporates absorbs heat from the portion of the substance which remains in a liquid state and hence, cools the liquid portion.

Finally, expansion or pressure reduction cooling refers to cooling which occurs when the pressure of a gas, liquid or a two-phase system is decreased by passing through a pressure reduction means. In one embodiment, this expansion means is a Joule-Thomson expansion valve. In another embodiment, the expansion means is either a hydraulic or gas expander. Because expanders recover work energy from the expansion process, lower process stream temperatures are possible upon expansion.

In one embodiment, the present invention employs a system for removing heavy hydrocarbon components such as benzene, cyclohexane, other aromatics, and/or higher molecular weight hydrocarbon species from a methane-based gas stream. The heavies removal system includes a heavies removal column and a Raman spectrometer. The heavies removal column is operable to perform both stripping and fractionating functions. The Raman spectrometer is a key component for controlling the operation of the heavies removal column to ensure optimal heavies removal.

The first step in removing heavies from the methane-based gas stream using the inventive heavies removal system is to cool the feed stream to the heavies removal column to a temperature such that about 0.1 to about 20 mole percent, preferably about 0.5 to about 10 mole percent, and most preferably 0.75 to 6 mole percent of the total gas stream is condensed, thereby forming a two-phased stream. The optimal mole percentage will depend upon the composition of the gas undergoing liquefaction and other process-related parameters readily ascertained by one possessing ordinary skill in the art. The two-phase stream is then fed to an upper section of the heavies removal column wherein the stream contacts a rising vapor stream from a lower portion of the column, thereby producing a heavies-rich liquid stream (typically NGL) which functions as a reflux stream and a heavies-depleted vapor stream which is produced from the column. As used herein, the term "heavies" will refer to any predominately organic compound possessing a molecular weight greater than propane. As used herein, the term "heavies-depleted stream" or "light hydrocarbon-rich stream" denotes a stream comprising predominately $C_1$–$C_3$ hydrocarbons, preferably predominately methane. As used herein, the term "heavy hydrocarbon-rich stream" or "heavies-rich stream" denotes a stream comprising predominately $C_4$+ hydrocarbons, such as benzene and cyclohexane.

The vapor stream introduced into the lower portion of the heavies removal column is referred to herein as a stripping gas stream. This stream preferably originates from an upstream location where the methane-based gas stream undergoing cooling has undergone some degree of cooling and liquids removal. Prior to introduction into the base of the column, the stripping gas is cooled via indirect contact with the heavies-rich liquid product produced from the bottom of the heavies removal column, thereby producing a warmed heavies-rich stream and a cooled stripping gas stream. The stripping gas may undergo partial condensation upon cooling and the resulting cooled stripping gas containing two phases may be fed directly to the column.

The temperature of the stripping gas entering the lower portion of the heavies removal column is generally greater than the temperature of the two-phase stream fed to the upper section of the heavies removal column. Thus, the temperature in the heavies removal column can be controlled by controlling the rate at which the stripping gas is charged to the column. The inventive heavies removal system employs a Raman spectrometer to measure the amount of heavies in the heavies-depleted (i.e., light-hydrocarbon rich) vapor stream produced from the heavies removal column. The Raman spectrometer is operably coupled to a flow controller which controls the rate of flow of the stripping gas stream to the heavies removal column. When the Raman spectrometer detects an excess quantity of heavies in the vapor stream produced from the column, the flow rate of the stripping gas to the column can be reduced to thereby reduce the temperature in the column and allow for improved heavies removal. If the Raman spectrometer detects little or no heavies in the heavies-depleted vapor stream produced from the column, the flow of the stripping gas to the column can be increased to thereby increase the temperature in the column and allow for optimal heavies removal with minimal lights removal.

In another embodiment of the present invention, one or more Raman spectrometers can be employed to determine at least one compositional property of the LNG stream produced by the LNG plant. Generally, the Raman spectrometer can be positioned immediately downstream of the final refrigeration cycle and immediately upstream of the LNG storage tank. The Raman spectrometer at this location can be used to determine the energy content (i.e., BTU content) of the LNG produced from the plant. Further, when two spaced-apart Raman spectrometers are employed at this location, a marker can be injected upstream of the Raman spectrometers and the flow rate of the LNG can be determined by detecting the presence of the marker in the LNG stream with each Raman spectrometer. The marker can subsequently be removed from the LNG via vaporization in the LNG storage tank.

Figure 1:
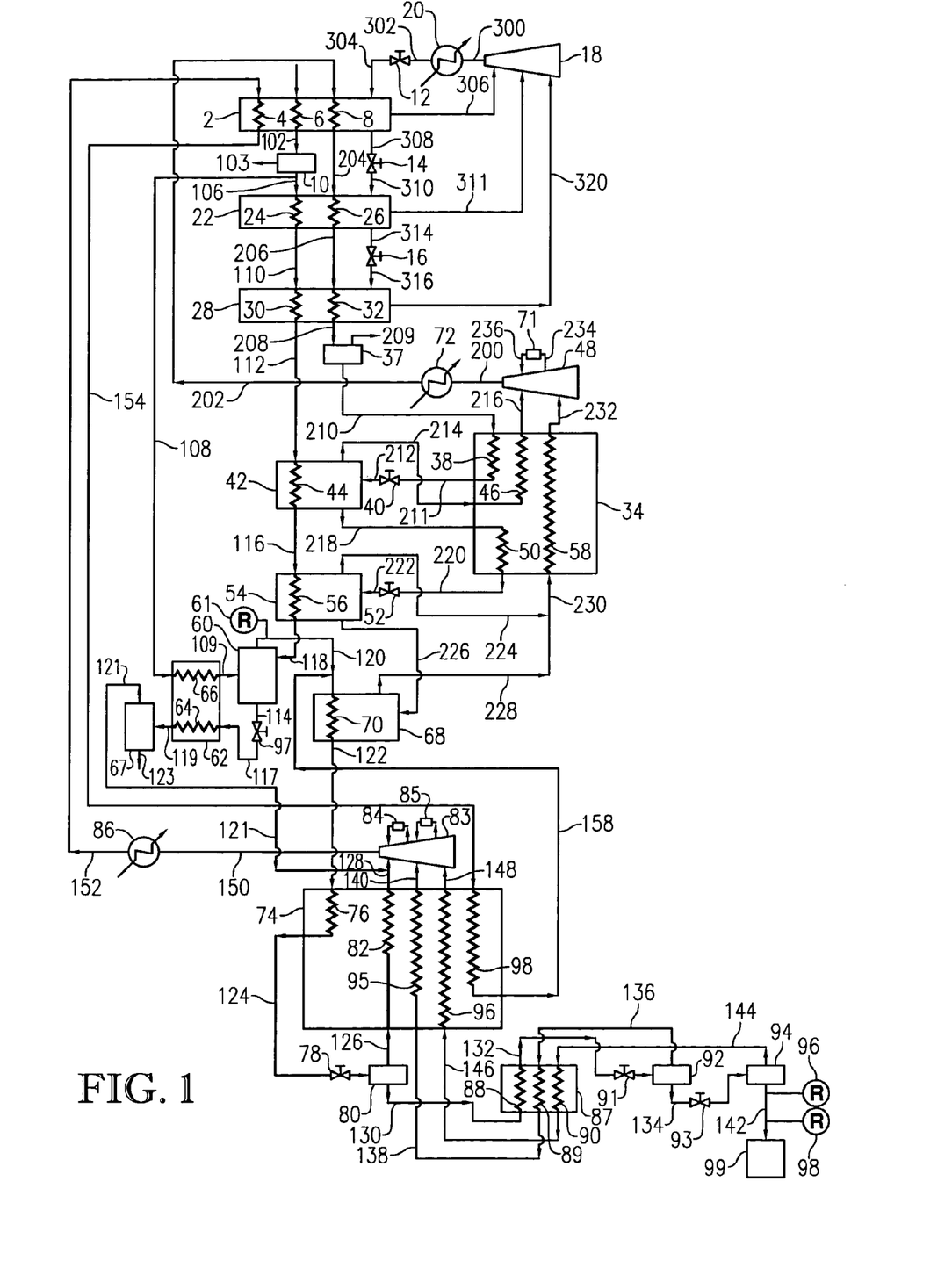
FIG. 1 is a simplified flow diagram of a cryogenic LNG production plant, particularly illustrating one embodiment of the present invention wherein a Raman spectrometer is implemented immediately downstream of the heavies removal column and a pair of Raman spectrometers are implemented immediately upstream of the LNG storage tank.

The flow schematic and apparatus set forth in FIG. 1 is a preferred embodiment of the open-cycle cascaded liquefaction process and is set forth for illustrative purposes. Those skilled in the art will also recognized that FIG. 1 is a schematic only and therefore, many items of equipment that would be needed in a commercial plant for successful operation have been omitted for the sake of clarity. Such items might include, for example, compressor controls, flow and level measurements and corresponding controllers, additional temperature and pressure controls, pumps, motors, filters, additional heat exchangers, valves, etc. These items would be provided in accordance with standard engineering practice.

To facilitate an understanding of FIG. 1, items numbered 1 through 99 depict process vessels and equipment directly associated with the liquefaction process. Items numbered 100 through 199 correspond to flow lines or conduits which contain methane in major portion. Items numbered 200 through 299 correspond to flow lines or conduits which contain the refrigerant ethylene or optionally, ethane. Items numbered 300 through 399 correspond to flow lines or conduits which contain the refrigerant propane. To the extent possible, the numbering system employed in FIG. 1 has been employed in FIGS. 2–5. In addition, the following numbering system has been added for additional elements not illustrated in FIG. 1. Items numbered 400 through 499 correspond to additional flow lines or conduits. Items numbered 500 through 599 correspond to additional process equipment such as vessels, columns, heat exchange means and valves, including process control valves. Items numbered 600 through 699 generally concern the process control system, exclusive of control valves, and specifically includes sensors, transducers, controllers and setpoint inputs. Items numbered 700 through 799 generally concern components associated with the Raman spectrometers used to determine at least one compositional property of a fluid stream flowing through a conduit.

Referring to FIG. 1, gaseous propane is compressed in a multistage compressor 18 driven by a gas turbine driver (not illustrated). The three stages of compression preferably exist in a single unit although each stage of compression may be a separate unit and the units mechanically coupled to be driven by a single driver. Upon compression, the compressed propane is passed through conduit 300 to a cooler 20 where it is liquefied. A representative pressure and temperature of the liquefied propane refrigerant prior to flashing is about 100° F. and about 190 psia. The stream from cooler 20 is passed through conduit 302 to a pressure reduction means, illustrated as expansion valve 12, wherein the pressure of the liquefied propane is reduced, thereby evaporating or flashing a portion thereof. The resulting two-phase product then flows through conduit 304 into a high-stage propane chiller 2 wherein gaseous methane refrigerant introduced via conduit 152, natural gas feed introduced via conduit 100, and gaseous ethylene refrigerant introduced via conduit 202 are respectively cooled via indirect heat exchange means 4, 6, and 8, thereby producing cooled gas streams respectively produced via conduits 154, 102, and 204. The gas in conduit 154 is fed to a main methane economizer 74 which will be discussed in greater detail in a subsequent section and wherein the stream is cooled via indirect heat exchange means 98. The resulting cooled compressed methane recycle stream produced via conduit 158 is then combined in conduit 120 with the heavies depleted (i.e., light-hydrocarbon rich) vapor stream from a heavies removal column 60 and fed to a methane condenser 68.

The propane gas from chiller 2 is returned to compressor 18 through conduit 306. This gas is fed to the high stage inlet port of compressor 18. The remaining liquid propane is passed through conduit 308, the pressure further reduced by passage through a pressure reduction means, illustrated as expansion valve 14, whereupon an additional portion of the liquefied propane is flashed. The resulting two-phase stream is then fed to an intermediate stage propane chiller 22 through conduit 310 thereby providing a coolant for chiller 22. The cooled feed gas stream from chiller 2 flows via conduit 102 to a knock-out vessel 10 wherein gas and liquid phases are separated. The liquid phase, which is rich in $C_3+$ components, is removed via conduit 103. The gaseous phase is removed and then split into two separate streams which are conveyed via conduits 106 and 108. The stream in conduit 106 is fed to propane chiller 22. The stream in conduit 108 becomes the feed to heat exchanger 62 and is ultimately the stripping gas to heavies removal column 60, discussed in more detail below. Ethylene refrigerant from chiller 2 is introduced to chiller 22 via conduit 204. In chiller 22, the feed gas stream, also referred to herein as a methane-rich stream, and the ethylene refrigerant streams are respectively cooled via indirect heat transfer means 24 and 26, thereby producing cooled methane-rich and ethylene refrigerant streams via conduits 110 and 206. The thus evaporated portion of the propane refrigerant is separated and passed through conduit 311 to the intermediate-stage inlet of compressor 18. Liquid propane refrigerant from chiller 22 is removed via conduit 314, flashed across a pressure reduction means, illustrated as expansion valve 16, and then fed to third stage chiller 28 via conduit 316.

As illustrated in FIG. 1, the methane-rich stream flows from intermediate-stage propane chiller 28 to the low-stage propane chiller/condenser 28 via conduit 110. In chiller 22, the stream is cooled via indirect heat exchange means 30. In a like manner, the ethylene refrigerant stream flows from the intermediate-stage propane chiller 22 to low-stage propane chiller/condenser 28 via conduit 206. In the latter, the ethylene refrigerant is totally condensed or condensed in nearly its entirety via indirect heat exchange means 32. The vaporized propane is removed from low-stage propane chiller/condenser 28 and returned to the low-stage inlet of compressor 18 via conduit 320.

As illustrated in FIG. 1, the methane-rich stream exiting low-stage propane chiller 28 is introduced to high-stage ethylene chiller 42 via conduit 112. Ethylene refrigerant exits low-stage propane chiller 28 via conduit 208 and is preferably fed to a separation vessel 37 wherein light components are removed via conduit 209 and condensed ethylene is removed via conduit 210. The ethylene refrigerant at this location in the process is generally at a temperature of about −24° F. and a pressure of about 285 psia. The ethylene refrigerant, via conduit 210, then flows to an ethylene economizer 34 wherein it is cooled via indirect heat exchange means 38 and removed via conduit 211 and passed to a pressure reduction means, illustrated as an expansion valve 40, whereupon the refrigerant is flashed to a preselected temperature and pressure and fed to high-stage ethylene chiller 42 via conduit 212. Vapor is removed from chiller 42 via conduit 214 and routed to ethylene economizer 34 wherein the vapor functions as a coolant via indirect heat exchange means 46. The ethylene vapor is then removed from ethylene economizer 34 via conduit 216 and feed to the high-stage inlet of ethylene compressor 48. The ethylene refrigerant which is not vaporized in high-stage ethylene chiller 42 is removed via conduit 218 and returned to ethylene economizer 34 for further cooling via indirect heat exchange means 50, removed from ethylene economizer via conduit 220, and flashed in a pressure reduction means, illustrated as expansion valve 52, whereupon the resulting two-phase product is introduced into a low-stage ethylene chiller 54 via conduit 222.

A methane-rich stream is removed from high-stage ethylene chiller 42 via conduit 116. This stream is then condensed in part via cooling provided by indirect heat exchange means 56 in low-stage ethylene chiller 54, thereby producing a two-phase stream which flows via conduit 118 to heavies removal column 60. As previously noted, the methane-rich stream in line 104 was split so as to flow via conduits 106 and 108. The contents of conduit 108, which is referred to herein as the stripping gas, is first fed to heat exchanger 62 wherein this stream is cooled via indirect heat exchange means 66 thereby becoming a cooled stripping gas stream which then flows by conduit 109 to heavies removal column 60. A heavies-rich liquid stream containing a significant concentration of $C_4+$ hydrocarbons, such as benzene, cyclohexane, other aromatics, and/or heavier hydrocarbon components, is removed from heavies removal column 60 via conduit 114, preferably flashed via a flow control means 97 which can also function as a pressure reduction means, preferably a control valve, and transported to heat exchanger 62 via by conduit 117. Preferably, the stream flashed via flow control means 97 is flashed to a pressure about or greater than the pressure at the high stage inlet port to methane compressor 83. Flashing also imparts greater cooling capacity to the stream. In heat exchanger 62, the stream delivered by conduit 117 provides cooling capabilities via indirect heat exchange means 64 and exits heat exchanger 62 via conduit 119. In heavies removal column 60, the two-phase stream introduced via conduit 118 is contacted with the cooled stripping gas stream introduced via conduit 109 in a countercurrent manner thereby producing a heavies-depleted vapor stream via conduit 120 and a heavies-rich liquid stream via conduit 117. A Raman spectrometer 61 is optically coupled to conduit 120 and is operable to measure at least one compositional property of the heavies-depleted, methane-rich vapor stream in conduit 120.

The heavies-rich stream in conduit 119 is subsequently separated into liquid and vapor portions or preferably is flashed or fractionated in vessel 67. In either case, a liquid stream rich in heavies is produced via conduit 123 and a second methane-rich vapor stream is produced via conduit 121. In the preferred embodiment, which is illustrated in FIG. 1, the stream in conduit 121 is subsequently combined with a second stream delivered via conduit 128, and the combined stream fed to the high pressure inlet port on the methane compressor 83 via conduit 140.

As previously noted, the gas in conduit 154 is fed to main methane economizer 74 wherein the stream is cooled via indirect heat exchange means 98. The resulting cooled compressed methane recycle or refrigerant stream in conduit 158 is combined in the preferred embodiment with the heavies-depleted vapor stream from heavies removal column 60, delivered via conduit 120, and fed to a low-stage ethylene condenser 68. In low-stage ethylene condenser 68, this stream is cooled and condensed via indirect heat exchange means 70 with the liquid effluent from low-stage ethylene chiller 54 which is routed to low-stage ethylene condenser 68 via conduit 226. The condensed methane-rich product from low-stage condenser 68 is produced via conduit 122. The vapor from low-stage ethylene chiller 54, withdrawn via conduit 224, and low-stage ethylene condenser 68, withdrawn via conduit 228, are combined and routed, via conduit 230, to ethylene economizer 34 wherein the vapors function as coolant via indirect heat exchange means 58. The stream is then routed via conduit 232 from ethylene economizer 34 to the low-stage side of ethylene compressor 48.

As noted in FIG. 1, the compressor effluent from vapor introduced via the low-stage side is removed via conduit 234, cooled via inter-stage cooler 71, and returned to compressor 48 via conduit 236 for injection with the high-stage stream present in conduit 216. Preferably, the two-stages are a single module although they may each be a separate module and the modules mechanically coupled to a common driver. The compressed ethylene product from the compressor is routed to a downstream cooler 72 via conduit 200. The product from cooler 72 flows via conduit 202 and is introduced, as previously discussed, to the high-stage propane chiller 2.

The liquefied stream in conduit 122 is generally at a temperature of about −125° F. and a pressure of about 600 psi. This stream passes via conduit 122 to main methane economizer 74, wherein the stream is further cooled by indirect heat exchange means 76 as hereinafter explained. From main methane economizer 74 the liquefied gas passes through conduit 124 and its pressure is reduced by a pressure reduction means, which is illustrated as expansion valve 78, which evaporates or flashes a portion of the gas stream. The flashed stream is then passed to a methane high-stage flash drum 80 where it is separated into a gas phase discharged through conduit 126 and a liquid phase discharged through conduit 130. The gas-phase is then transferred to main methane economizer 74 via conduit 126 wherein the vapor functions as a coolant via indirect heat transfer means 82. The vapor exits main methane economizer 74 via conduit 128 where it is combined with the gas stream delivered by conduit 121. These streams are then fed to the high pressure inlet port of methane compressor 83.

The liquid phase in conduit 130 is passed through a second methane economizer 87 wherein the liquid is further cooled by downstream flash vapors via indirect heat exchange means 88. The cooled liquid exits second methane economizer 87 via conduit 132 and is expanded or flashed via pressure reduction means, illustrated as expansion valve 91, to further reduce the pressure and, at the same time, vaporize a second portion thereof. This flash stream is then passed to an intermediate-stage methane flash drum 92 where the stream is separated into a gas phase passing through conduit 136 and a liquid phase passing through conduit 134. The gas phase flows through conduit 136 to second methane economizer 87 wherein the vapor cools the liquid introduced to economizer 87 via conduit 130 via indirect heat exchanger means 89. Conduit 138 serves as a flow conduit between indirect heat exchange means 89 in second methane economizer 87 and indirect heat transfer means 95 in main methane economizer 74. This vapor leaves main methane economizer 74 via conduit 140 which is connected to the intermediate stage inlet on methane compressor 83.

The liquid phase exiting intermediate stage flash drum 92 via conduit 134 is further reduced in pressure by passage through a pressure reduction means, illustrated as a expansion valve 93. Again, a third portion of the liquefied gas is evaporated or flashed. The fluids from expansion valve 93 are passed to a final or low stage flash drum 94. In flash drum 94, a vapor phase is separated and passed through conduit 144 to second methane economizer 87 wherein the vapor functions as a coolant via indirect heat exchange means 90, exits second methane economizer 87 via conduit 146, which is connected to the first methane economizer 74 wherein the vapor functions as a coolant via indirect heat exchange means 96, and ultimately leaves main methane economizer 74 via conduit 148 which is connected to the low pressure port on compressor 83.

The liquefied natural gas product from flash drum 94 which is at approximately atmospheric pressure is passed through conduit 142 to a LNG storage tank 99. An upstream Raman spectrometer 96 and a downstream Raman spectrometer 98 are optically coupled to conduit 142. Each Raman spectrometer 96, 98 is operable to measure at least one compositional property of the LNG flowing through conduit 142. The operation of Raman spectrometers 96, 98 will be discussed in more detail below with reference to FIG. 5.

The low pressure, low temperature LNG boil-off vapor stream from the storage unit and optionally, the vapor returned from the cooling of the rundown lines associated with the LNG loading system, is preferably recovered by combining such stream or streams with the low pressure flash vapors present in either conduits 144, 146, or 148; the selected conduit being based on a desire to match vapor stream temperatures as closely as possible.

As shown in FIG. 1, the high, intermediate, and low stages of compressor 83 are preferably combined as single unit. However, each stage may exist as a separate unit where the units are mechanically coupled together to be driven by a single driver. The compressed gas from the low-stage section passes through an inter-stage cooler 85 and is combined with the intermediate pressure gas in conduit 140 prior to the second-stage of compression. The compressed gas from the intermediate stage of compressor 83 is passed through an inter-stage cooler 84 and is combined with the high pressure gas in conduit 140 prior to the third-stage of compression. The compressed gas is discharged from the high-stage methane compressor through conduit 150, is cooled in cooler 86, and is routed to high pressure propane chiller 2 via conduit 152, as previously discussed.

FIG. 1 depicts the expansion of the liquefied phase using expansion valves with subsequent separation of gas and liquid portions in the chiller or condenser. While this simplified scheme is workable and utilized in some cases, it is often more efficient and effective to carry out partial evaporation and separation steps in separate equipment, for example, an expansion valve and separate flash drum might be employed prior to the flow of either the separated vapor or liquid to a propane chiller. In a like manner, certain process streams undergoing expansion are ideal candidates for employment of a hydraulic expander as part of the pressure reduction means thereby enabling the extraction of work energy and also lower two-phase temperatures.

With regard to the compressor/driver units employed in the process, FIG. 1 depicts individual compressor/driver units (i.e., a single compression train) for the propane, ethylene and open-cycle methane compression stages. However in a preferred embodiment for any cascaded process, process reliability can be improved significantly by employing a multiple compression train comprising two or more compressor/driver combinations in parallel in lieu of the depicted single compressor/driver units. In the event that a compressor/driver unit becomes unavailable, the process can still be operated at a reduced capacity.

Figure 2:
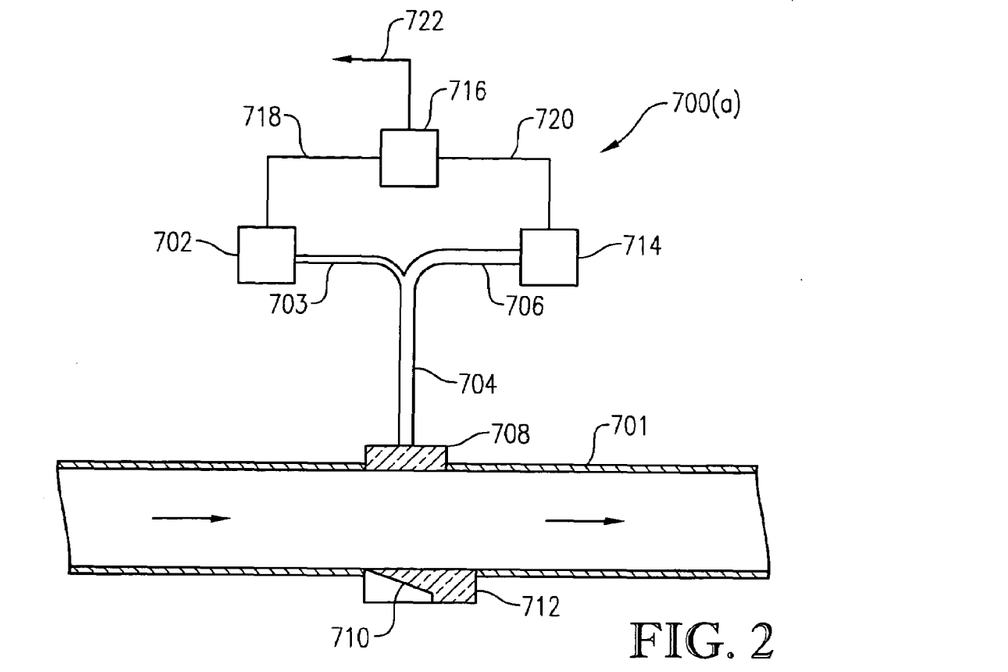
FIG. 2 is a partial sectional side view schematically illustrating a first Raman spectrometer configuration operable to measure at least one compositional property of a fluid stream flowing through a conduit without removing the fluid stream from the conduit.

Referring now to FIG. 2, a first Raman spectrometer configuration 700(a) is illustrated as measuring at least one compositional property of the fluid stream flowing through conduit 701. Such a Raman spectrometer configuration can be employed in the LNG facility shown in FIG. 1 at any or all of the locations designated Raman spectrometer 61, 96, 98. First Raman spectrometer configuration 700(a) includes a laser source 702 for producing light having an excitation wavelength. Although conventional diode lasers can be used as laser source 702, it is presently preferred to use an external cavity diode laser. The light output from the external cavity diode laser can be controlled to provide a powerful, yet stable light output compared to a typical single mode diode laser. Laser source 702 is optically coupled to an excitation optical fiber 703 which is combined with one or more collection optical fibers 706 to form a bundle of optical fibers 704. Fiber bundle 704 can be optically coupled to conduit 701 via a transparent window 708 in conduit 701. While a fluid stream, generally a cooled natural gas stream, is flowing through conduit 701, the light emitted from excitation optical fiber 703 is shined into/on the flowing fluid. A colored glass filter 710 can be employed opposite of window 708 to absorb light having the excitation wavelength. Filter 710 can be optically coupled to conduit 120 via a transparent window 712. Filter 710 is preferably oriented on a slight angle to minimize the amount of reflected laser light which enters collection fibers 706 of fiber bundle 704. Raman scattered light emanating from within conduit 701 enters collection optical fibers 706 of fiber bundle 704. The scattered light collected via collection fibers 706 is conducted to a spectrometer 714. The exit ends of collection fibers 706 are preferably aligned in a linear array so that a linear optical signal is generated. In spectrometer 714, a conventional charge coupled device converts the collected optical signal into a corresponding collected electrical signal 720. In computing device 716 collected electrical signal 720 is compared with an excitation signal 718 (corresponding to the excitation light) from laser source 700. By comparing signal 718 and signal 720, computing device 716 can generate a Raman signal 722 indicative of the measured amount of at least one chemical constituent in the stream flowing through conduit 701.

Figure 3:
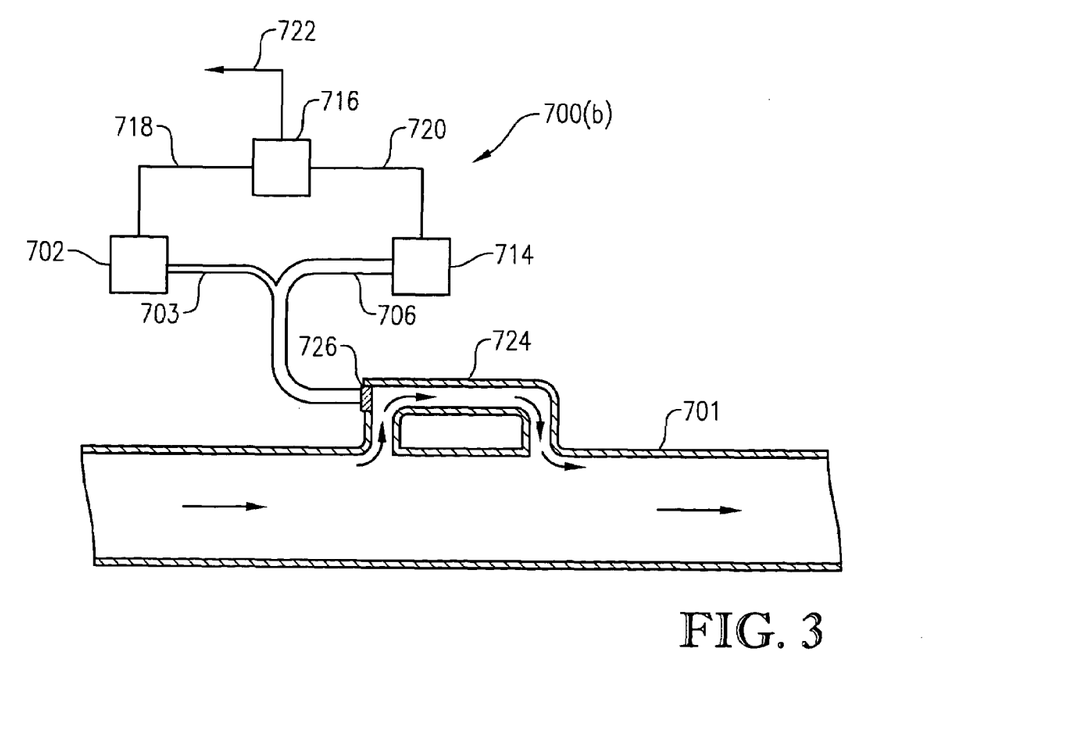
FIG. 3 is a partial sectional side view schematically illustrating a second Raman spectrometer configuration operable to measure at least one compositional property of a fluid stream flowing through the conduit without removing the fluid stream from the conduit.

Referring to FIG. 3, a second Raman spectrometer configuration 700(b) employs a sample tube 724 to collect compositional data from the fluid stream in conduit 701. Such a Raman spectrometer configuration can be employed in the LNG facility shown in FIG. 1 at any or all of the locations designated Raman spectrometer 61, 96, 98. Second Raman spectrometer configuration 700(b) is similar to the first Raman spectrometer configuration 700(a) (shown in FIG. 2); however, a portion of the fluid stream flowing through conduit 701 is continuously routed through sample tube 124. Optical fiber bundle 704 is optically coupled to sample tube 724 via a transparent lens 726. While the fluid stream is flowing through sample tube 724, light from excitation fiber 703 is directed into sample tube 724. The Raman scattered light emanating from sample tube 724 is transported from sample tube 724 to spectrometer 714 via collection optical fibers 706. Because sample tube 724 is fluidly coupled to conduit 120 in a manner which allows the fluid stream flowing in conduit 701 to continuously flow through sample tube 724 with little or no change in temperature and pressure, sample tube 724 is considered to be part of conduit 701. Thus, for purposes of defining the present invention, the systems illustrated in FIGS. 2 and 3 allow the fluid stream to be analyzed without removing it from conduit 701. There are numerous advantages to being able to measure compositional properties of the fluid stream without removing it from the conduit. In particular, the temperature and pressure of the analyzed fluid stream is substantially the same as the temperature and pressure of the fluid stream flowing through the conduit. This allows for a more accurate compositional analysis. Further, the ability to continuously analyze a flowing fluid stream in real time allows for more accurate control of components whose operating parameters depend upon the composition of the fluid stream.

Figures 4, 5:
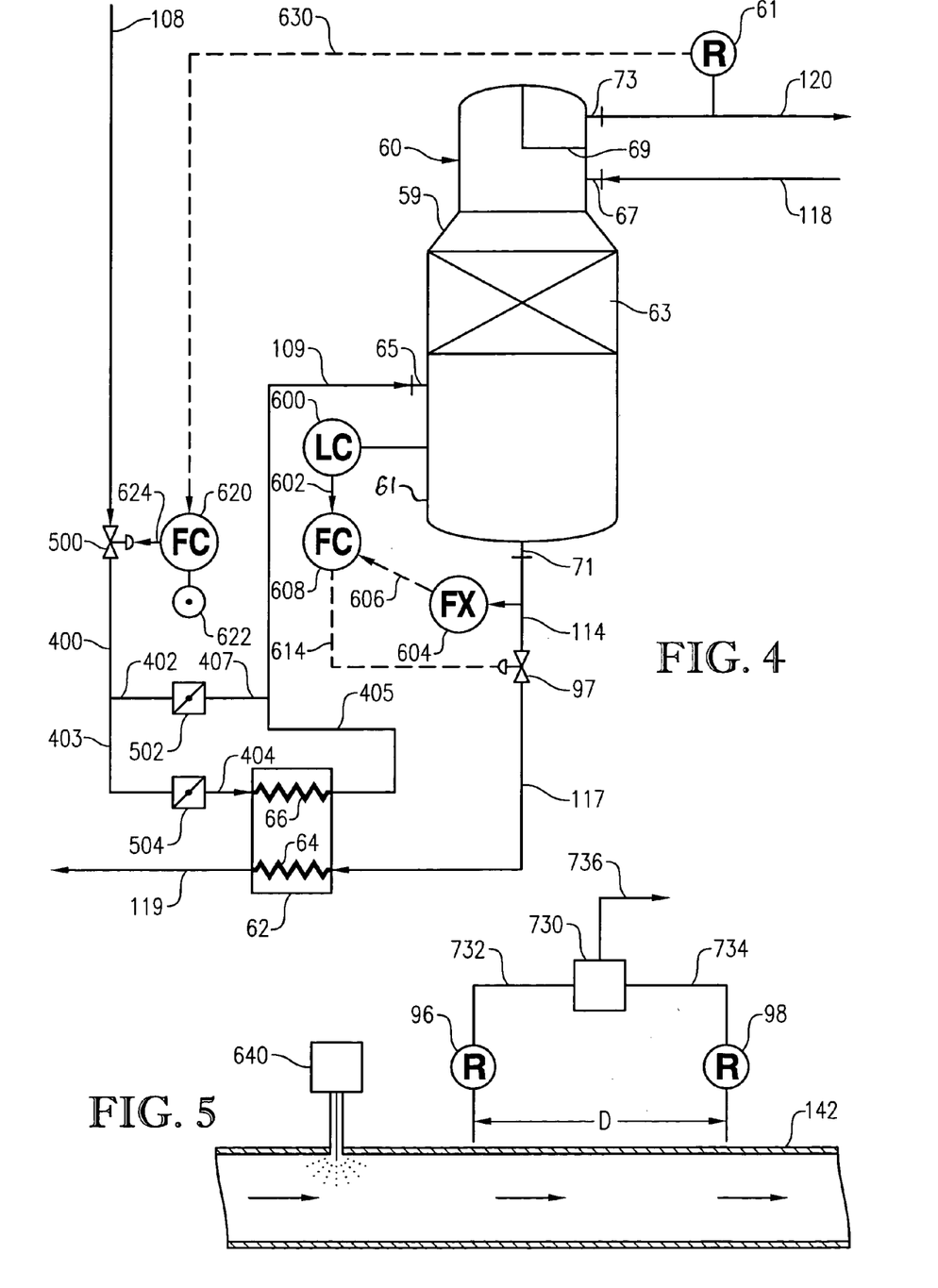
FIG. 4 is an enlarged view of one embodiment of the heavies removal system (schematically shown in FIG. 1), particularly illustrating a heavies removal column control system employing a Raman spectrometer located at the light hydrocarbon outlet of the heavies removal column, wherein the output of the Raman spectrometer can be employed to manipulate the flow rate of a stripping gas to the heavies removal column.
FIG. 5 is an enlarged representation of the pair of Raman spectrometers coupled to the conduit carrying LNG to the storage tank (schematically shown in FIG. 1), particularly illustrating a marker injector fluidly coupled to the conduit upstream of the Raman spectrometers.

Referring to FIG. 4, a preferred heavy hydrocarbon removal system, suitable for use in the LNG facility illustrated in FIG. 1, is illustrated as employing a Raman spectrometer 61 to more accurately control the system. As discussed above with reference to FIG. 1, a two-phase stream is delivered to a feed inlet 67 of heavies removal column 60 via conduit 118. The stream entering heavies removal column 60 is preferably a cooled natural gas stream comprising predominately methane. More preferably the stream entering heavies removal column 60 comprises at least 75 mole percent methane. The temperature of the natural gas entering heavies removal column 60 is preferably less than about −25° F., more preferably less than about −50° F., and most preferably between −50° F. and −80° F. From an operational perspective, the length of conduit 118 should be sufficient to ensure adequate mixing of the two phases of the feed stream such that equilibrium conditions are approached. The amount of liquids in the two-phase stream in conduit 118 is preferably controlled via maintaining the streams at a desired temperature.

The stripping gas stream is delivered to a stripping gas inlet 65 of heavies removal column 60 via conduit 109. Although depicted in FIG. 1 as originating from the feed gas stream from the first stage of propane cooling, this stripping gas stream can originate from any location within the process or may be an outside methane-rich stream. As illustrated in FIG. 4, at least a portion of the stripping gas undergoes cooling in heat exchanger 62 via indirect heat exchange means 66 prior to entering inlet 65 of column 60. It is preferred for the stripping gas to be cooled a natural gas comprising predominately methane. Preferably, the stripping gas comprises at least 75 mole percent methane. The temperature of the stripping gas entering heavies removal column 60 at stripping gas inlet 65 should be different than the temperature of the feed stream entering heavies removal column 60 at feed inlet 67. Preferably, the temperature of the stripping gas entering heavies removal column 60 at stripping gas inlet 65 is at least 5° F. warmer than the temperature of the feed entering heavies removal column 60 at feed inlet 67, more preferably at least 10° F. warmer, and most preferably at least 20° F. warmer. This difference between the temperature of the stripping gas and the feed gas allows the temperature in heavies removal column 60 to be adjusted by adjusting the flow rate of the stripping gas to heavies removal column 60.

Heavies removal column 60 generally includes a vessel shell 61, internal packing 63, and a gas liquid separator 69. Feed inlet 67 is disposed generally above packing 63, while stripping gas inlet 65 is disposed generally below packing 63. Packing 63 can be plates and/or trays suitable to provide 2 to 15 theoretical stages, preferably 3 to 10 theoretical stages, still more preferably 4 to 8 theoretical stages, and most preferably about 5 theoretical stages. Gas/liquid separator 69 is disposed between feed inlet 67 and lights outlet 73 and can be any conventional separation means known in the art for demisting or removing entrained liquids from a vapor stream. In heavies removal column 60, the feed stream and the stripping gas stream are separated into a heavies-rich stream, which exits column 60 via heavies outlet 71, and a heavies-depleted stream (i.e., lights-rich stream), which exits column 60 via lights outlet 73.

As illustrated in FIG. 4, the heavies-rich streamed exiting heavies removal column 60 via heavies via outlet 71 is conducted to a control valve 97 via conduit 114. The heavies-rich stream is then conducted to heat exchanger 62, via conduit 117, wherein the heavies-rich stream is heated in heat exchange means 64. The heated heavies-rich stream then exits heat exchanger 62 via conduit 119. In the preferred embodiment, illustrated in FIG. 1, the heated heavies-rich stream is feed to a demethanizer 67. The flowrate of the heavies-rich liquid from column 60 may be controlled via various methodologies readily available to one skilled in the art. The control apparatus illustrated in FIG. 4 is a preferred apparatus and is comprised of a level controller device 600, also a sensing device, and a signal transducer connected to the level controller device 600, operably located in the lower section of column 60. The controller 600 establishes an output signal 602 that either typifies the flowrate in conduit 114 required to maintain a desired level in column 60 or indicates that the actual level has exceeded a predetermined level. A flow measurement device and transducer 604 operably located in conduit 114 establishes an output signal 606 that typifies the actual flowrate of the fluid in conduit 114. The flow measurement device is preferably located upstream of the control valve so as to avoid sensing a two-phase stream. Signal 602 is provided as a set point signal to flow controller 608. Signals 602 and 606 are respectively compared in flow controller 608 and controller 608 establishes an output signal 614 responsive to the difference between signals 602 and 606. Signal 614 is provided to control valve 97, and valve 97 is manipulated responsive to signal 614. A setpoint signal (not illustrated) representative of a desired level in column 60 may be manually inputted to level controller 600 by an operator or in the alternative, be under computer control via a control algorithm. Depending on the operating conditions, operator or computing machine logic is employed to determine whether control will be based on liquid level or flowrate. In response to the variable flowrate input of signal 606 and the selected setpoint signal, controller 608 provides an output signal 614 which is responsive to the difference between the respective input and setpoint signals. This signal is scaled so as to be representative, as the case may be, of the position of the control valve 97 required to maintain the flowrate of fluid substantially equal to the desired flowrate or the liquid level substantially equal to the desired liquid level, as the case may be.

In heat exchanger 62, the heavies-rich stream in heat exchange means 64 cools the stripping gas stream flowing through heat exchange means 66. The degree to which the stripping gas is cooled by the heavies-bearing stream prior to entry into the column may be controlled via various methodologies readily available to one skilled in the art. In one embodiment, the entire stripping gas stream is fed to the heat exchanger and the degree of cooling controlled by such parameters as the amount of heavies-rich liquid stream made available for heat transfer, the heat transfer surface areas available for heat transfer, and/or the residence times of the fluids undergoing heating or cooling as the case may be. In a preferred embodiment, the stripping gas stream delivered via conduit 108 flows through control valve 500 into conduit 400 whereupon the stream is split and transferred via conduits 402 and 403. The stream flowing through conduit 403 ultimately flows through indirect heat transfer means 66 in heat exchanger 62. A means for manipulating the relative flowrates of fluid in conduits 402 and 403 is provided in either conduits 402 or 403 or both. The means illustrated in FIG. 4 are simple hand control valves, designated 502 and 504, which are respectively attached to conduits 404 and 407. However, a control valve whose position is manipulated by a controller and for which input to the controller is comprised of a setpoint and signal representative of flow in the conduit, such as that discussed above for the heavies-bearing stream, may be substituted for one or both of the hand control valves. In any event, the valves are operated such that the temperature approach difference of the streams in conduits 117 and 404 to heat exchanger 62 does not exceed 50° F. whereupon damage to the heat exchanger might result. The cooled stripping gas leaves indirect heat transfer means 66 via conduit 405 and is combined at a junction point with uncooled methane-rich stripping gas delivered via conduit 407 thereby forming the cooled methane-rich stripping gas stream which is delivered to heavies removal column 60 via conduit 109.

The heavies-depleted stream exits heavies removal column 60 at lights outlet 73. As shown in FIG. 1, the heavies-depleted stream is then preferably conducted to low-stage ethylene condenser 68 via conduit 120. The heavies-depleted stream in conduit 120 preferably has a temperature of less than about 0° F., more preferably less than about −50° F., and most preferably less than −100° F. Operably located in conduit 120 is a Raman spectrometer 61 which generates an output signal 630 that indicates the measured amount of heavies in the heavies-depleted fluid stream in conduit 120. Raman spectrometer 61 can be configured similar to the Raman spectrometer systems 700(*a*) and 700(*b*) illustrated in FIGS. 2 and 3, respectively. In one embodiment, Raman spectrometer 61 measures the amount of benzene in the heavies-depleted stream flowing through conduit 120, and signal 630 is indicative of this measured amount of benzene. Signal 630 is provided as a process variable input to a flow controller/computing device 620. Also provided either manually or via computer output is a set point value for the amount of heavies in the fluid stream in conduit 120 represented by signal 622. When Raman spectrometer 61 is used to measure this amount of benzene in conduit 120, the set point is preferably 2 to 20 ppmw benzene, more preferably 4 to 8 ppmw benzene. The flow controller then provides an output signal 624 which is responsive to the difference between the respective input and setpoint signals and which is scaled to be representative of the position of flow control valve 500 required to maintain the desired flowrate in conduit 109.

When Raman spectrometer 61 indicates that an access amount of heavy-hydrocarbon components are present in the light hydrocarbon-rich stream in conduit 120, controller 620 causes flow control valve 500 to decrease the flow of the stripping gas entering heavies removal column 60 via conduit 109. Because the stripping gas entering heavies removal column 60 via conduit 109 is warmer than the feed stream charged to heavies removal column 60 via conduit 118, decreasing the flow rate of the stripping gas to heavies removal column 60 decreases the temperature in heavies removal column 60, thereby reducing the amount of heavies which exits heavies removal column 60 via lights outlet 73. When Raman spectrometer 61 detects virtually no heavies in conduit 120, controller 620 can increase the flow of the stripping gas through conduit 109 into heavies removal column 60. Increasing the flow of the stripping gas into heavies removal column 60 causes an increase in temperature in heavies removal column 60 which allows more heavy hydrocarbons to exit heavies removal column 60 via lights outlet 73. Thus, because Raman spectrometer 61 can continuously monitor even trace amounts of heavies present in the light hydrocarbon-rich stream in conduit 120, the proper temperature in heavies removal column 60 can be maintained to thereby optimize heavies removal without substantial removal of non-heavy hydrocarbons.

The controllers previously discussed may use various well-known modes of control such as proportional, proportional-integral, or proportional-integral-derivative (PID). In the preferred embodiments for temperature and flow control, a proportional-integral controller is utilized, but any controller capable of accepting two input signals and producing a scaled output signal, representative of a comparison of the two input signals, is within the scope of the invention. The operation of PID controllers is well known in the art. Essentially, the output signal of a controller may be scaled to represent any desired factor or variable. One example is where a desired temperature and an actual temperature are compared by a controller. The controller output could be a signal representative of a change in the flow rate of some fluid necessary to make the desired and actual temperatures equal. On the other hand, the same output signal could be scaled to represent a percentage, or could be scaled to represent a pressure change required to make the desired and actual temperatures equal.

Referring now to FIG. 5, an enlarged view of conduit 142 (show in FIG. 1 as extending between flash drum 94 and LNG storage tank 99) is illustrated as having spaced-apart Raman spectrometers 96, 98 optically coupled thereto, as well as a marker injector 640 fluidly coupled thereto. Raman spectrometers 96, 98 are spaced along conduit 142 and separated by a distance "D". First and second Raman spectrometers 96, 98 can be of a similar configuration to those shown in FIGS. 2 and 3. Thus, Raman spectrometers 96, 98 can read at least one compositional property of the fluid stream flowing through conduit 142 without removing the fluid stream from conduit 142. The fluid stream in conduit 142 preferably has a temperature of less than −25° F., more preferably less than about −50° F., and most preferably less than −100° F. Preferably, the fluid stream in conduit 142 is LNG at about atmospheric pressure.

As shown in FIG. 5, marker injector 640 is located upstream of Raman spectrometers 96, 98. Marker injector 640 is operable to inject a marker composition into the fluid stream (preferably LNG). Raman spectrometers 96, 98 are operable to detect the presence of the marker injected by injector 640. When first Raman spectrometer 96 detects the presence of the marker, a first signal 732 is sent to a computing device 730. When second Raman spectrometer 98 detects the presence of the marker, a second signal 734 is sent to computing device 730. Computing device 730 includes a internal clock which can compute the time lapse between when the first and second Raman spectrometers 96, 98 first indicate the presence of the marker in the fluid stream. The distance "D" between Raman spectrometers 96, 98 can then be divided by the time elapsed between detection of the marker by Raman spectrometers 96, 98, to thereby compute a measure velocity of the fluid stream in conduit 142. A signal 736 indicating the computed velocity can then be outputted and used to calculate flow rate-dependent production parameters. The marker injected into conduit 142 via injector 640 can be any composition that is easily detected by Raman spectrometers 96, 98 and readily removable from the fluid stream in conduit 142. Preferably, the marker has a boiling point that is lower than the boiling point of the fluid stream in conduit 42 so that it can be readily phase separated from the LNG. Most preferably, the marker is nitrogen.

Figure 6:
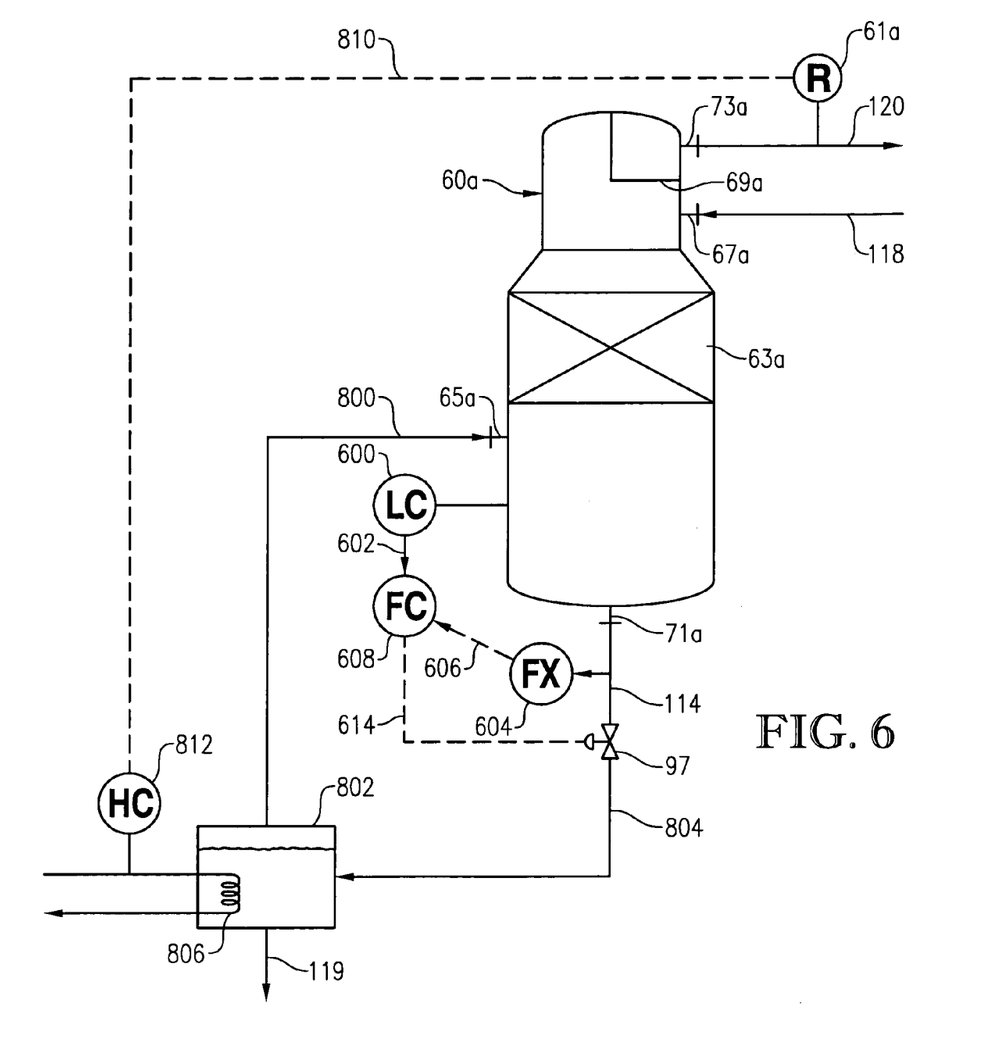
FIG. 6 is an enlarged view of another embodiment of the heavies removal system (schematically shown in FIG. 1), particularly illustrating a heavies removal column control system employing a Raman spectrometer located at the light hydrocarbon outlet of the heavies removal column, wherein the output of the Raman spectrometer can be employed to manipulate the flow rate of a stripping gas that originates from and returns to the heavies removal column.

FIG. 6 illustrates a heavies removal column 60a similar to the heavies removal column 60 illustrated in FIG. 4. However, in FIG. 6, a different configuration is employed to provide the stripping gas to stripping gas inlet 65a. The configuration illustrated in FIG. 6 utilizes the heavies stream exiting heavies removal column 60a via heavies outlet 71a to generate the stripping gas that enters heavies removal column 60a via stripping gas inlet 65a. As shown in FIG. 6, the heavies stream from heavies outlet 71a is conducted via conduit 804 to a reboiler 802, wherein the liquid heavies stream is heated with a heating mechanism 806. The heat added by heating mechanism 806 in reboiler 802 vaporizes a portion of the liquids heavy stream introduced via conduit 804. The vaporized heavies are removed from reboiler 802 and conducted to stripping gas inlet 65a via conduit 800. The liquid heavies stream is removed from reboiler 802 via conduit 119. Thus, the stripping gas stream employed in heavies removal column 61a is simply a vaporized portion of the heavies stream exiting the bottom of heavies removal column 60a.

The amount of stripping gas provided to heavies removal column 60a can be adjusted by controlling the amount of heat imparted via heating mechanism 806. Heating mechanism 806 can be any mechanism operable to heat the liquid in reboiler 802. In one embodiment, heating mechanism 806 contains a heated fluid that flows through tubular coils in reboiler 802 to thereby heat the liquids contained in reboiler 802 via indirect heat exchange. In another embodiment, heating mechanism 806 is an electrical heating element.

A Raman spectrometer 61a can be operably coupled to conduit 120 to measure the amount of heavies in the heavies-depleted fluid stream in conduit 120. Raman spectrometer 61a can generate a signal 810 that is input into a heat controller 812. Heat controller 812 varies the amount of heat imparted to reboiler 802 by heating mechanism 806. When heating mechanism 806 is an electrical resistive heating element, heat controller 812 can control the electrical current through the heating element to thereby control the amount of heat imparted to reboiler 802. When heating mechanism 806 is a tubular coil with a heated fluid flowing therethrough, heat controller 812 can control the flow rate and/or temperature of the fluid flowing therethrough. In either case, when Raman spectrometer 61a indicates that an excess amount of heavy-hydrocarbon components are present in the light hydrocarbon-rich stream in conduit 120, heat controller 812 causes a decrease in the amount of heat provided by heating mechanism 806. This decreased amount of heat in reboiler 802 reduces the amount of vapor generated therein and thereby reduces the flow of the stripping gas entering heavies removal column 60a via stripping gas inlet 65a. When Raman spectrometer 61a detects virtually no heavies in conduit 120, heat controller 812 can increase the amount of heat provided to reboiler 802 by heating mechanism 806. This increase in heating causes more of the liquid in reboiler 802 to be vaporized, thereby increasing the flow of stripping gas to stripping gas inlet 65a.

Figure 7:
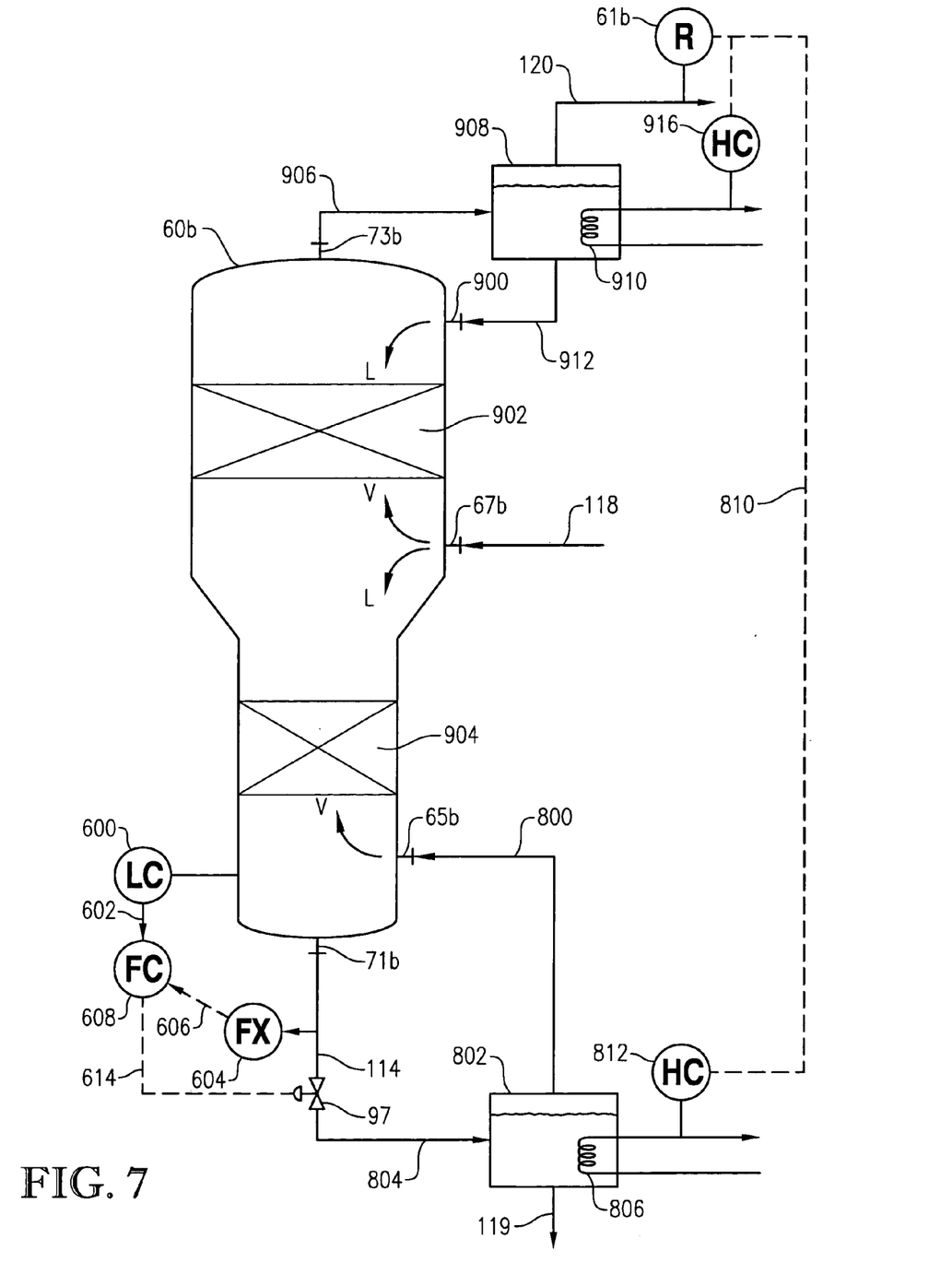
FIG. 7 is an enlarged view of yet another embodiment of the heavies removal system (schematically shown in FIG. 1), particularly illustrating a heavies removal column control system employing a Raman spectrometer located at the light hydrocarbon outlet of the heavies removal column, wherein the output of the Raman spectrometer can be employed to manipulate the flow rate of a reflux stream that originates from and returns to the heavies removal column.

Referring now to FIG. 7, a different configuration for a heavies removal column 60b is illustrated. Heavies removal column 60b of FIG. 7 is a refluxed heavies removal column that includes two sets of internal packing 902 and 904. The two-phase feed stream enters heavies removal column 60b via feed inlet 67b. It is preferred for feed inlet 67b to be located between upper packing 902 and lower packing 904. The stripping gas stream 800 is provided by the reboiler system described above with reference to FIG. 6. The stripping gas stream enters heavies removal column 60b via stripping gas inlet 65b. It is preferred for stripping gas inlet 65b to be located below lower packing 904. Heavies removal column 60b also includes a reflux inlet 900, which is disposed above upper packing 902. The heavies-depleted stream exiting lights outlet 73b is conducted via conduit 906 to a condenser/separator 908. Condenser/separator 908 is equipped with a condensing mechanism 910. Condensing mechanism 910 is operable to cause condensing of at least a portion of the heavies-depleted stream entering condenser 908. The condensed liquids from condenser 908 are conducted to reflux inlet 900 via conduit 912. The uncondensed lights exit condenser 908 via conduit 120. As discussed above with reference to FIG. 6, a Raman spectrometer 61b can be operably coupled to conduit 120 in order to control the stripping gas stream provided to heavies removal column 60 via conduit 800. In addition, the heavies content measurement provided by Raman spectrometer 808 can be used as an input to controller 916, which controls the amount of condensing provided in condenser 908. When Raman spectrometer 61b indicates an excess in the amount of heavies in conduit 120, the degree of condensing provided in condenser 908 can be increased to thereby increase the liquid reflux stream provided to heavies removal column 60b via conduit 112. When Raman spectrometer 61b detects virtually no heavies in the stream in conduit 120, the amount of condensing provided by condenser 908 can be reduced to thereby reduce the flow of the reflux stream to heavies removal column 60b.

In accordance with one embodiment of the present invention, Raman spectrometers 96, 98, can also be used to measure a various compositional properties of the fluid stream and conduit 142. The various measured compositional properties detected by Raman spectrometers 96, 98 can then be used to compute (via computing device 730) the energy content (i.e., BTU content) of the fluid stream in conduit 142. Alternatively, Raman spectrometers 96, 98 can be used to determine stream quality properties, such as Saybolt color.

While specific cryogenic methods, materials, items of equipment and control instruments are referred to herein, it is to be understood that such specific recitals are not to be considered limiting but are included by way of illustration and to set forth the best mode in accordance with the present invention. Further, while only three locations for Raman spectrometers are illustrated in FIG. 1, it should be understood that the Raman spectrometers could be used at a variety of locations in the LNG facility to measure properties of cooled fluid streams.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A method of liquefying natural gas, said method comprising the steps of:
   (a) cooling the natural gas to thereby produce a cooled natural gas having a temperature of less than about −25° F.;
   (b) transporting the cooled natural gas in a conduit; and
   (c) while the cooled natural gas is flowing through the conduit, using a Raman spectrometer to measure at least one property of the cooled natural gas without removing the cooled natural gas from the conduit.

2. The method according to claim 1,
said cooled natural gas having a temperature of less than about −50° F.

3. The method according to claim 1,
said cooled natural gas having a temperature of less than about −100° F.

4. The method according to claim 1,
said cooled natural gas being primarily in the liquid phase.

5. The method according to claim 1,
said Raman spectrometer being configured to direct a beam of light onto the cooled natural gas without removing the cooled natural gas from the conduit.

6. The method according to claim 1,
step (c) including using the Raman spectrometer to determine the amount of at least one hydrocarbon contained in the cooled natural gas stream.

7. The method according to claim 6,
step (c) including using the Raman spectrometer to determine the amount of benzene or cyclohexane in the cooled natural gas stream.

8. The method according to claim 1,
step (c) including using the Raman spectrometer to determine the energy content of the cooled natural gas.

9. The method according to claim 1; and
   (d) injecting a marker into the conduit upstream of the location where the Raman spectrometer measures said at least one property of the cooled natural gas,
   step (c) including using the Raman spectrometer to detect the presence of the marker in the cooled natural gas.

10. The method according to claim 9,
said marker having a lower boiling point than the cooled natural gas.

11. The method according to claim 9,
said marker comprising predominately nitrogen.

12. The method according to claim 1; and
   (e) vaporizing the liquefied natural gas produced via steps (a)–(c).

13. A method of separating a heavy hydrocarbon from a light hydrocarbon, said method comprising the steps of:
   (a) charging a hydrocarbon-containing stream comprising the heavy hydrocarbon and the light hydrocarbon to a separator;
   (b) in the separator, separating the hydrocarbon-containing stream into a light hydrocarbon-rich stream and a heavy hydrocarbon-rich stream;
   (c) using a Raman spectrometer to analyze the light hydrocarbon-rich stream and determine a measured heavy hydrocarbon value indicative of the amount of the heavy hydrocarbon in the light hydrocarbon-rich stream; and (d) adjusting at least one operating parameter of the separator in response to the measured heavy hydrocarbon value.

14. The method according to claim 13,
step (d) including adjusting the temperature in the separator.

15. The method according to claim 13; and
(e) between steps (c) and (d), comparing the measured heavy hydrocarbon value to a predetermined heavy hydrocarbon value.

16. The method according to claim 15,
step (d) including reducing the temperature in the separator when the measured heavy hydrocarbon value is greater than the predetermined heavy hydrocarbon value,
step (d) including increasing the temperature in the separator when the measured heavy hydrocarbon value is less than the predetermined heavy hydrocarbon value.

17. The method according to claim 13; and
(f) simultaneously with step (a), charging a stripping gas to the separator.

18. The method according to claim 17,
step (d) including adjusting the flow rate of the stripping gas charged to the separator to thereby effect a temperature change in the separator.

19. The method according to claim 18,
said stripping gas having substantially the same composition as the hydrocarbon-containing stream,
said stripping gas having a temperature that is at least 5° F. different from the temperature of the hydrocarbon-containing stream.

20. The method according to claim 13,
step (b) including separating the hydrocarbon-containing stream by distillation.

21. The method according to claim 13,
step (c) being performed while the analyzed light hydrocarbon-rich stream is flowing through a conduit,
step (c) being performed without removing the analyzed light hydrocarbon-rich stream from the conduit.

22. The method according to claim 13,
said hydrocarbon-containing stream comprising predominately the light hydrocarbon,
said light hydrocarbon being a $C_1$–$C_3$ hydrocarbon,
said heavy hydrocarbon being a $C_4$+ hydrocarbon.

23. The method according to claim 22,
said light hydrocarbon being methane,
said heavy hydrocarbon being benzene or cyclohexane.

24. The method according to claim 22,
said hydrocarbon-containing stream comprising predominately natural gas,
said heavy hydrocarbon-rich stream comprising predominately natural gas liquids.

25. The method according to claim 24,
said light hydrocarbon-rich stream being at a temperature of less than about −25° F. when analyzed by the Raman spectrometer in step (c).

26. A method of measuring the velocity of a fluid stream flowing through a conduit, said method comprising the steps of:
(a) injecting a marker into the fluid stream flowing through the conduit at an injection location;

(b) using a first Raman spectrometer to detect the presence of the marker in the fluid stream at a first measurement location downstream of the injection location; and (c) using a second Raman spectrometer to detect the presence of the marker in the fluid stream at a second measurement location downstream of the first measurement location.

27. The method according to claim 26,
steps (b) and (c) being performed without removing the fluid stream from the conduit.

28. The method according to claim 26,
step (b) including determining a first time indicating the time at which the presence of the marker in the fluid stream is detected by the first Raman spectrometer,
step (c) including determining a second time indicating the time at which the presence of the marker in the fluid stream is detected by the second Raman spectrometer.

29. The method according to claim 28; and
(d) calculating the flow velocity of the fluid stream by dividing the distance between the first and second measurement locations by the time lapse between the first and second times.

30. The method according to claim 26,
said fluid stream comprising predominately liquefied natural gas.

31. The method according to claim 30,
said marker comprising a fluid composition having a lower boiling point than the liquefied natural gas.

32. The method according to claim 30,
said marker comprising predominately nitrogen.

33. The method according to claim 26; and
(e) using at least one of the first and second Raman spectrometers to detect the presence of at least one composition other than the marker in the fluid stream.

34. The method according to claim 33,
step (e) including using said at least one of the first or second Raman spectrometers to determine the amount of methane, ethane, or propane in the fluid stream.

35. The method according to claim 33,
step (e) including using said at least one of the first or second Raman spectrometers to determine the energy content of the fluid stream.

36. A method of controlling a heavies removal column in a liquefied natural gas plant, said method comprising the steps of:
(a) charging a natural gas stream comprising a light hydrocarbon and a heavy hydrocarbon to the heavies removal column;
(b) simultaneously with step (a), charging a stripping gas stream to the heavies removal column;
(c) in the heavies removal column, separating the natural gas stream into a light hydrocarbon-rich stream and a heavy hydrocarbon-rich stream;
(d) using a Raman spectrometer to determine a measured heavy hydrocarbon value indicative of the amount of the heavy hydrocarbon in the light hydrocarbon-rich stream; and
(e) adjusting the flow rate of the stripping gas to the heavies removal column in response to the measured heavy hydrocarbon value.

37. The method according to claim 36,
said stripping gas stream being at least 5° F. warmer than the natural gas stream entering the heavies removal column,
said natural gas stream entering the heavies removal column having a temperature of less than about −25° F.

38. The method according to claim 37,
said stripping gas stream comprising predominately natural gas.

39. The method according to claim 38,
said natural gas stream entering the heavies removal column comprising at least about 75 mole percent methane,
said heavy hydrocarbon being a $C_4+$ hydrocarbon.

40. The method according to claim 39,
said heavy hydrocarbon being benzene or cyclohexane.

41. The method according to claim 36; and
(f) upstream of the heavies removal column, cooling the natural gas stream in a first refrigeration cycle employing a first refrigerant comprising predominately propane.

42. The method according to claim 41; and
(g) downstream of the heavies removal column, cooling the light hydrocarbon-rich stream in an open methane cycle.

43. The method according to claim 42; and
(h) downstream of the first refrigeration cycle and upstream of the heavies removal column, cooling the natural gas stream in a second refrigeration cycle employing a second refrigerant comprising predominately ethane or ethylene.

44. The method according to claim 36,
said heavies removal column including a vessel shell and a packed section disposed in the vessel shell,
said stripping gas entering the heavies removal column at a location generally below the packed section,
said natural gas entering the heavies removal column at a location generally above the packed section,
said light hydrocarbon-rich stream exiting the heavies removal column at a location generally above the packed section,
said heavy hydrocarbon-rich stream exiting the heavies removal column generally below the packed section.

45. An apparatus for liquefying natural gas, said apparatus comprising:
a final refrigeration cycle for producing liquefied natural gas at a temperature of less than about −25° F.;
a conduit for carrying the produced liquefied natural gas away from the final refrigeration cycle; and
a first Raman spectrometer coupled to the conduit and operable to measure at least one compositional property of the liquefied natural gas without removing the liquefied natural gas from the conduit.

46. The apparatus according to claim 45,
said first Raman spectrometer including a means for directing light onto the liquefied natural gas flowing in the conduit.

47. The apparatus according to claim 46,
said first Raman spectrometer including a means for detecting light reflected or refracted by the liquefied natural gas flowing in the conduit.

48. The apparatus according to claim 47,
said first Raman spectrometer including a means for comparing the light directed onto the liquefied natural gas to the light reflected or refracted by the liquefied natural gas to determine said at least one compositional property of the liquefied natural gas.

49. The apparatus according to claim 45; and
a second Raman spectrometer coupled to the conduit downstream of the first Raman spectrometer and operable to measure at least one compositional property of the liquefied natural gas without removing the liquefied natural gas from the conduit.

50. The apparatus according to claim 49; and
an injector for injecting a marker into the conduit upstream of the first Raman spectrometer,
said first and second Raman spectrometers being operable to detect the presence of the marker in the liquefied natural gas.

51. The apparatus according to claim 50; and
a computing device operably coupled to the first and second Raman spectrometers,
said computing device including a timer.

52. The apparatus according to claim 51,
said computing device being operable to determine the flow rate of the liquefied natural gas flowing through the conduit based on the elapsed time between detection of the marker by the first Raman spectrometer and detection of the marker by the second Raman spectrometer.

53. An apparatus for liquefying natural gas, said apparatus comprising:
a heavies removal column operable to remove at least one heavy hydrocarbon from the natural gas;
a stripping gas conduit fluidly coupled to the heavies removal column and operable to deliver a stripping gas to the heavies removal column;
a flow controller operable to control the flow of the stripping gas to the heavies removal column;
a Raman spectrometer disposed downstream of the heavies removal column and operable to detect the heavy hydrocarbon in the natural gas stream and generate a signal indicative of the amount of the heavy hydrocarbon in the natural gas stream; and
an automatic control device operably coupled to the flow controller and the Raman spectrometer,
said automatic control device being programmed to adjust the flow controller in response to the signal generated by the Raman spectrometer.

54. The apparatus according to claim 53,
said heavies removal column including a vessel shell and an internal packed section disposed in the vessel shell,
said heavies removal column including a natural gas inlet above the packed section for receiving the natural gas,
said heavies removal column including a stripping gas inlet below the packed section for receiving the stripping gas,
said heavies removal column including a natural gas outlet above the packed section for discharging the natural gas,
said heavies removal column including a heavies outlet below the packed section for discharging the heavy hydrocarbon removed from the natural gas.

55. The apparatus according to claim 53; and
an initial refrigeration cycle employing an initial refrigerant to cool the natural gas stream; and
a final refrigeration cycle employing a final refrigerant to cool the natural gas stream,
said heavies removal column being disposed downstream of the initial refrigeration cycle and upstream of the final refrigeration cycle.

56. The apparatus according to claim 55,
said stripping gas conduit being operable to conduct a portion of the natural gas stream from a location upstream of the first refrigeration cycle to the heavies removal column, thereby allowing the stripping gas to bypass the first refrigeration cycle.

57. The apparatus according to claim 56,
said initial refrigerant comprising predominately propane or propylene.

58. The apparatus according to claim 57,
said final refrigerant comprising predominately methane.

59. The apparatus according to claim 58; and
an intermediate refrigeration cycle employing an intermediate refrigerant to cool the natural gas stream,
said intermediate refrigerant comprising predominately ethylene or ethane,
said final refrigeration cycle being an open methane cycle.

60. The apparatus according to claim 59,
said intermediate refrigeration cycle including a high stage heat exchanger for cooling the natural gas and a low stage heat exchanger for cooling the natural gas,
said heavies removal column being disposed downstream of the high stage heat exchanger and upstream of the low stage heat exchanger.

61. The method according to claim 13,
wherein the temperature and/or pressure of said light hydrocarbon-rich stream during analysis by said Raman spectrometer is substantially the same as the temperature and/or pressure of said light hydrocarbon-rich stream upon exiting said separator.

62. The method according to claim 36,
wherein the temperature and/or pressure of said light hydrocarbon-rich stream during measurement by said Raman spectrometer is substantially the same as the temperature and/or pressure of said light hydrocarbon-rich stream upon exiting said heavies removal column.

63. The apparatus according to claim 53,
wherein said Raman spectrometer is operable to detect said heavy hydrocarbon in said natural gas stream while said natural gas stream is at substantially the same temperature and/or pressure as the temperature and/or pressure of said natural gas stream upon exiting said heavies removal column.

* * * * *